United States Patent [19]

Baltes et al.

[11] Patent Number: 4,522,800
[45] Date of Patent: Jun. 11, 1985

[54] PROCESS FOR THE PRODUCTION OF A CRYSTALLINE ALUMINOSILICATE ZEOLITE

[75] Inventors: Herbert Baltes, Frankfurt am Main; Heinz Litterer, Wiesbaden; Ernst I. Leupold, Neu-Anspach; Friedrich Wunder, Flörsheim am Main, all of Fed. Rep. of Germany

[73] Assignee: Hoechst Aktiengesellschaft, Frankfurt am Main, Fed. Rep. of Germany

[21] Appl. No.: 491,860

[22] Filed: May 5, 1983

[30] Foreign Application Priority Data

May 8, 1982 [DE] Fed. Rep. of Germany ....... 3217322

[51] Int. Cl.$^3$ .............................................. C01B 33/20
[52] U.S. Cl. .................................... 423/329; 423/328; 423/330; 502/77
[58] Field of Search ............... 423/328, 329, 333, 332; 502/77, 62

[56] References Cited

U.S. PATENT DOCUMENTS

| | | | |
|---|---|---|---|
| 2,950,952 | 8/1960 | Breck et al. | 423/329 |
| 3,947,482 | 3/1976 | Albers et al. | 423/329 |
| 4,086,186 | 4/1978 | Rubin et al. | 423/328 |
| 4,242,233 | 12/1980 | Ball et al. | 423/328 |
| 4,377,502 | 3/1983 | Klotz | 423/328 |
| 4,407,728 | 10/1983 | Ball et al. | 423/328 |

FOREIGN PATENT DOCUMENTS

| | | |
|---|---|---|
| 1131206 | 9/1982 | Canada . |
| 0002900 | 7/1979 | European Pat. Off. . |
| 0055529 | 7/1982 | European Pat. Off. . |
| 0057049 | 8/1982 | European Pat. Off. . |
| 2749024 | 5/1978 | Fed. Rep. of Germany . |
| 2924870 | 1/1980 | Fed. Rep. of Germany . |
| 1365318 | 8/1974 | United Kingdom ............. 423/329 |
| 202356A | 6/1980 | United Kingdom . |
| 2079735 | 1/1982 | United Kingdom ............. 423/328 |

OTHER PUBLICATIONS

L. W. Staples et al., Mineralogical Magazine, 32, 261–281, (1959).
R. M. Barrer FRS, *Hydrothermal Chemistry of Zeolites*, Academic Press, New York, 1982, pp. 204–205, 247.
A. Erdem & L. B. Sand, in "Proceedings of the 5th International Conference on Zeolites", (Ed. L. V. C. Rees), p. 64, Heyden London, 1980.

*Primary Examiner*—Gary P. Straub
*Assistant Examiner*—Jackson Leeds
*Attorney, Agent, or Firm*—Curtis, Morris & Safford

[57] ABSTRACT

A method for making crystalline aluminosilicate ZSM-34 zeolites, useful as catalysts for making $C_2$–$C_4$-olefins from methanol, from a reaction mixture containing silicon, aluminum, sodium, potassium, and an organic template compound which is (i) a salt of an ammonium compound of di-, tri-, or tetra-ethanolamine or (ii) a mixture of at least one of diethanolamine and triethanolamine with certain lower alkanols, lower alkylene diols, or lower alkyl iodides, sulfates, or p-toluenesulfonates.

3 Claims, No Drawings

PROCESS FOR THE PRODUCTION OF A CRYSTALLINE ALUMINOSILICATE ZEOLITE

Zeolites are, in particular, crystalline aluminosilicates in which ordered structures containing cavities and pores are formed as a result of three-dimensional linking of $SiO_4$ and $AlO_4$ tetrahedra. In the hydrated state, these pores and cavities are filled with water. This can be removed or replaced by other molecules, without the crystal structure being affected. The negative charges on the $AlO_4$ tetrahedra are compensated by cations. These can, if desired, be exchanged for other cations. The properties described make it possible to use the zeolites as ion exchangers, adsorbents and catalysts (D. W. Breck: Zeolite Molecular Sieves, 1974).

Zeolites of the X, Y, mordenite, erionite and offretite types, for example, are of considerable industrial interest as catalysts for transformation reactions of hydrocarbons, such as cracking, hydrocracking or isomerization. Zeolites of the pentasil type (e.g. zeolite ZSM-5) are becoming increasingly important as catalysts for converting methanol to hydrocarbons.

Because of the very large number of possible uses as catalysts, there is considerable interest in novel zeolites having specific catalytic properties.

The invention relates to crystalline aluminosilicate zeolites which (a) contain silicon, aluminum, sodium, potassium and an organic ammonium compound in the following ratio, expressed as molar ratios of oxides:

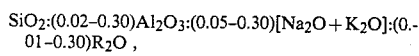

where R designates an ammonium radical of the general formula $(HOCH_2CH_2)_4N$, $(HOCH_2CH_2)_3R^1N$ or $(HOCH_2CH_2)_2R^1R^2N$, and the radicals $R^1$ and $R^2$ can be identical or different and denote alkyl, substituted alkyl, cycloalkyl, substituted cycloalkyl, aryl, substituted aryl or hydrogen, and (b) exhibit the characteristic signals listed in Table 1 in the X-ray diffraction diagram:

TABLE 1

| Interplanar spacings d[Å] | Relative intensity $I/I_0$ |
|---|---|
| 11.5 ± 0.3 | strong to very strong |
| 9.2 ± 0.2 | weak |
| 7.6 ± 0.2 | weak to medium |
| 6.6 ± 0.1 | medium to strong |
| 6.3 ± 0.1 | weak |
| 5.7 ± 0.1 | weak |
| 5.35 ± 0.1 | weak |
| 4.56 ± 0.1 | weak to medium |
| 4.32 ± 0.1 | strong |
| 4.16 ± 0.1 | weak |
| 3.81 ± 0.1 | medium to strong |
| 3.75 ± 0.1 | strong to very strong |
| 3.59 ± 0.1 | strong to very strong |
| 3.30 ± 0.1 | medium |
| 3.15 ± 0.1 | medium |
| 2.86 ± 0.1 | strong to very strong |
| 2.80 ± 0.1 | weak to medium |
| 2.67 ± 0.1 | weak to medium |
| 2.49 ± 0.1 | weak to medium |

In this table, $I_0$ denotes the intensity of the strongest signal.

The following values apply to the intensity data in Table 1:

| Relative intensity | 100 $I/I_0$ |
|---|---|
| very strong | 80–100 |
| strong | 50–80 |
| medium | 20–50 |
| weak | 0–20 |

Preferably, the zeolites according to the invention possess the following composition, expressed as molar ratios of the oxides:

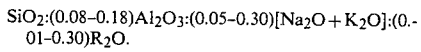

In this formula, R has the meaning given above, and is preferably $(HOCH_2CH_2)_3R^1N$.

$R^1$ and $R^2$ have the above meaning, and are preferably alkyl radicals, each having a maximum of five carbon atoms, or hydrogen, in particular methyl, ethyl or hydrogen. $R^1$ and $R^2$ can be different, but preferably $R^1 = R^2$, in particular $R^1 = R^2 =$ methyl.

The novel zeolites according to the invention possess a structure which is similar to that of erionite [cf. L. W. Staples et al., Mineralogical Magazine 32 (1959) 261] or of the synthetic zeolites T (U.S. Pat. No. 2,950,952) and ZSM-34 (German Offenlegungsschrift No. 2,749,024), but differ from these in composition, adsorption properties and catalytic behavior.

The zeolites according to the invention can be prepared by mixing an ammonium compound RX with aluminum compounds, silicon compounds, sodium compounds, potassium compounds and water, and heating the mixture in a sealed vessel. In the above formula, R has the meaning given above. It is also possible to add seed crystals to the mixture before it is heated.

The starting compounds are employed in general in the following ratio, expressed as molar ratios of the oxides:

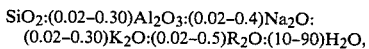

preferably in the ratio

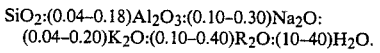

Any water-soluble salt of R can be employed as the ammonium compound RX. X can denote, for example: hydroxyl, chloride, bromide, iodide, sulfate, phosphate, sulfonate, carboxylate, carbonate and sulfite.

The ammonium compound RX can be employed in the absence of a solvent. However, it is preferably produced in situ in the reaction mixture by using, on the one hand, a mixture of triethanolamine and/or diethanolamine and, on the other hand, a compound of the general formula $R^1Y$ where $R^1$ has the above meaning. Y is in general hydroxyl, monoalkyl sulfate, halide or sulfonate, in particular hydroxyl.

$R^1Y$ is preferably methanol, ethanol, propanol, butanol, ethylene glycol, 1,2-propylene glycol, dimethyl sulfate, diethyl sulfate, methyl iodide, ethyl iodide, propyl iodide, methyl p-toluenesulfonate, ethyl p-toluenesulfonate or propyl p-toluenesulfonate. In particular, $R^1Y$ is methanol, ethanol or ethylene glycol. The molar ratio of $R^1Y$ to amine (triethanolamine and/or diethanolamine) is in general from 0.5 to 20, preferably 1 to 10, in particular 4 to 10.

The zeolites according to the invention can also be prepared, with satisfactory crystallinity, in the absence of a compound of the general formula $R^1Y$, i.e. in the presence of only triethanolamine and/or diethanolamine.

Examples of silicon, aluminum, sodium and potassium compounds which can be employed are: silica gel, potassium silicate, sodium silicate, sodium aluminate, potassium aluminate, aluminum halides, aluminum metahydroxide, potassium hydroxide, potassium sulfate, potassium halides, sodium hydroxide, sodium sulfate and sodium halides. However, other silicon, aluminum, potassium and sodium compounds are also suitable for the preparation of the zeolites according to the invention.

A mixture of the particular selected compounds with water is heated in general for 18 to 1,000 hours, preferably 24 to 500 hours, at a temperature between 80° and 200° C., preferably between 110° and 160° C., in a sealed vessel.

The zeolites formed are isolated in a customary manner, for example by filtration, and are washed and dried. They can be converted to the catalytically active forms by known methods, e.g. by calcination and/or ion exchange (D. W. Breck, Zeolite Molecular Sieves, 1974).

After they have been converted to the catalytically active forms, the zeolites according to the invention are distinguished in particular by high selectivity and by a low level of coking in the conversion of methanol to lower olefins. It is surprising that it is at all possible to obtain zeolites having the features according to the invention with the aid of the stated method.

The examples which follow are intended to illustrate the invention, but are not intended to restrict it in any way. All X-ray diffraction data given were recorded using a computer-controlled D-500 powder diffractometer from Siemens. Copper $K\alpha$ radiation was used.

EXAMPLE 1

11.2 g of sodium aluminate (54% by weight of $Al_2O_3$ and 41% by weight of $Na_2O$), 5.9 g of sodium hydroxide, 5.3 g of potassium hydroxide, 48.7 g of triethanolamine and 31 g of methanol are dissolved in 150 ml of water. 117 g of 40% strength by weight of colloidal silica gel are introduced into this solution. The resulting mixture is homogenized, and heated for 226 hours at 140° C. in a sealed vessel. The product formed is filtered off, washed with water and dried at 120° C.

The product has the X-ray diffraction pattern reproduced in Table 2.

Chemical analysis gives the following composition, expressed as molar ratios of the oxides:

$$SiO_2:0.139Al_2O_3:0.069Na_2O:0.086K_2O:0.057R_2O,$$

where R is 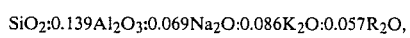 $(HOCH_2CH_2)_3NCH_3$.

TABLE 2

| Interplanar spacings d[Å] | Relative intensity 100 I/I$_0$ |
| --- | --- |
| 11.4 | 93 |
| 9.1 | 4 |
| 7.54 | 15 |
| 6.58 | 68 |
| 6.27 | 6 |
| 5.70 | 4 |
| 5.33 | 3 |
| 4.98 | 4 |
| 4.55 | 12 |
| 4.31 | 56 |

TABLE 2-continued

| Interplanar spacings d[Å] | Relative intensity 100 I/I$_0$ |
| --- | --- |
| 4.16 | 5 |
| 3.81 | 26 |
| 3.75 | 100 |
| 3.57 | 67 |
| 3.30 | 23 |
| 3.14 | 45 |
| 2.92 | 3 |
| 2.86 | 61 |
| 2.84 | 78 |
| 2.81 | 18 |
| 2.67 | 24 |
| 2.50 | 5 |

EXAMPLE 2

11.2 g of sodium aluminate (54% by weight of $Al_2O_3$ and 41% by weight of $Na_2O$), 5.9 g of sodium hydroxide, 5.3 g of potassium hydroxide and 97.4 g of triethanolamine are dissolved in 150 ml of water. 117 g of 40% by weight colloidal silica gel and 0.5 g of seed crystals from Example 1 are introduced into this solution. The resulting mixture is homogenized, and heated for 192 hours at 150° C. in a sealed vessel. The product formed is filtered off, washed with water and dried at 120° C. for 24 hours.

The product gives the X-ray signals shown in Table 1. Some of the product was calcined for 24 hours at 540° C. The X-ray diffraction pattern of the calcined product is reproduced in Table 3. It possesses the following chemical composition, expressed as molar ratios of the oxides:

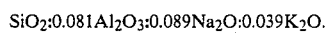
$$SiO_2:0.081Al_2O_3:0.089Na_2O:0.039K_2O.$$

TABLE 3

| Interplanar spacings d[Å] | Relative intensity 100 I/I$_0$ |
| --- | --- |
| 11.3 | 74 |
| 9.1 | 5 |
| 7.53 | 15 |
| 6.56 | 56 |
| 6.25 | 4 |
| 5.69 | 4 |
| 5.32 | 3 |
| 4.54 | 10 |
| 4.30 | 56 |
| 4.16 | 7 |
| 3.80 | 25 |
| 3.73 | 100 |
| 3.55 | 66 |
| 3.28 | 22 |
| 3.14 | 33 |
| 2.86 | 51 |
| 2.83 | 75 |
| 2.65 | 16 |
| 2.46 | 16 |

EXAMPLE 3

2.24 g of sodium aluminate, 1.2 g of sodium hydroxide, 1.1 g of potassium hydroxide, 9.7 g of triethanolamine and 12 g of ethylene glycol are dissolved in 30 ml of water. 23.4 g of 40% strength by weight colloidal silica gel are introduced into this solution. The resulting mixture is homogenized, and heated for 336 hours at 110° C. After the mixture has been worked up as in Example 1, the crystalline product whose X-ray diffraction data correspond to those given in Table 1 is obtained.

Chemical analysis gives the following composition, expressed as molar ratios of the oxides:

$SiO_2:0.106Al_2O_3:0.041Na_2O:0.044K_2O:0.048R_2O$, where R is $(HOCH_2CH_2)_4N$.

EXAMPLE 4

11.2 g of sodium aluminate, 5.9 g of sodium hydroxide, 5.3 g of potassium hydroxide, 34.3 g of diethanolamine and 62 g of methanol are dissolved in 150 ml of water. 117 g of 40% strength by weight colloidal silica gel are introduced into this solution. The resulting mixture is homogenized, and heated for 192 hours at 150° C. in a sealed vessel. The product formed is filtered off, washed with water and dried at 140° C. The product has the X-ray diffraction pattern shown in Table 1.

EXAMPLE 5

2.0 g of sodium aluminate, 1.0 g of sodium hydroxide, 1.0 g of potassium hydroxide, 14.6 g of triethanolamine and 9.0 g of ethanol are dissolved in 30 ml of water. 24.0 g of 40% strength by weight colloidal silica gel are introduced into this solution. The resulting mixture is homogenized, and heated for 192 hours at 150° C. After the mixture has been worked up as in Example 1, the crystalline product whose X-ray data correspond to those shown in Table 1 is obtained.

EXAMPLE 6

2.24 g of sodium aluminate, 1.2 g of sodium hydroxide, 1.1 g of potassium hydroxide, 9.7 g of triethanolamine and 8.3 g of dimethyl sulfate are dissolved in 30 ml of water. 23.4 g of 40% strength by weight colloidal silica gel and 0.5 g of seed crystals from experiment 1 are introduced into this solution. The resulting mixture is homogenized, and heated for 192 hours at 160° C. After the mixture has been worked up as in Example 1, the crystalline product whose X-ray data correspond to those shown in Table 1 is obtained.

We claim:

1. A method for making a crystalline aluminosilicate zeolite which
   (a) contains silicon, aluminum, sodium, and potassium in the following ratio, expressed as a molar ratio of oxides, $SiO_2:(0.02-0.30)Al_2O_3:(0.05-0.30)[Na_2O+K_2O]$, (b) exhibits the following characteristic signals in its X-ray diffraction diagram as synthesized

TABLE 1

| Interplanar spacings d[Å] | Relative intensity I/I₀ |
| --- | --- |
| 11.5 ± 0.3 | strong to very strong |
| 9.2 ± 0.2 | weak |
| 7.6 ± 0.2 | weak to medium |
| 6.6 ± 0.1 | medium to strong |
| 6.3 ± 0.1 | weak |
| 5.7 ± 0.1 | weak |
| 5.35 ± 0.1 | weak |
| 4.56 ± 0.1 | weak to medium |
| 4.32 ± 0.1 | strong |
| 4.16 ± 0.1 | weak |
| 3.81 ± 0.1 | medium to strong |
| 3.75 ± 0.1 | strong to very strong |
| 3.59 ± 0.1 | strong to very strong |
| 3.30 ± 0.1 | medium |
| 3.15 ± 0.1 | medium |
| 2.86 ± 0.1 | strong to very strong |
| 2.80 ± 0.1 | weak to medium |
| 2.67 ± 0.1 | weak to medium |
| 2.49 ± 0.1 | weak to medium | where $I_0$ denotes the intensity of the strongest signal, which method comprises heating, in a sealed vessel, at a temperature from 80° C. to 200° C., for a time between 18 hours and 1000 hours, a reaction mixture of water and compounds of silicon, aluminum, sodium, potassium, and of an organic template agent having the following initial composition expressed as a molar ratio, $SiO_2:(0.02-0.30)Al_2O_3:(0.02-0.40)Na_2O:(0.02-0.30)K_2O:$ (0.04–1.00) of the organic template agent (10–90)$H_2O$, and then calcining the crystalline zeolite so made to destroy said organic template agent said organic template agent being provided as (i) an ammonium compound of the formula RX wherein R is an ammonium cation of the formula $(HOCH_2CH_2)_4N^+$, $(HOCH_2CH_2)_3R^1N^+$, or $(HOCH_2CH_2)_2R^1R^2N^+$ and $R^1$ and $R^2$, which are the same or different, are hydrogen or alkyl having up to 5 carbon atoms, and X is hydroxy, chloride, bromide, iodide, sulfate, phosphate, sulfonate, carboxylate, carbonate, or sulfite, or as (ii) a mixture of one molar part of at least one of diethanolamine and triethanolamine with from one to 10 molar parts of methanol, ethanol, propanol, butanol, ethylene glycol, 1,2-propylene glycol, dimethyl sulfate, diethyl sulfate, methyl iodide, ethyl iodide, propyl iodide, methyl p-toluenesulfonate, ethyl p-toluenesulfonate, or propyl p-toluenesulfonate.

2. A method as in claim 1 wherein said reaction mixture has the composition $SiO_2:(0.04-0.18)Al_2O_3:(0.10-0.30)Na_2O:(0.04-0.20)K_2O:(0.20-0.80)$ of the organic template compound: (10–40) $H_2O$.

3. A method as in claim 1 wherein said agent is a mixture of at least one of diethanolamine and triethanolamine with methanol, ethanol, or ethylene glycol.

* * * * *

UNITED STATES PATENT AND TRADEMARK OFFICE
CERTIFICATE OF CORRECTION

PATENT NO. : 4,522,800
DATED : June 11, 1985
INVENTOR(S) : Baltes et al.

It is certified that error appears in the above-identified patent and that said Letters Patent is hereby corrected as shown below:

Column 6, lines 29 to 31, change

"$K_2O$:
(0.04-1.00) of the organic template agent (10-90)$H_2O$," to

--$K_2O$:(0.04-1.00) of the organic template agent: (10-90)$H_2O$,--

Signed and Sealed this

Fourth Day of February 1986

[SEAL]

Attest:

DONALD J. QUIGG

Attesting Officer  Commissioner of Patents and Trademarks